United States Patent [19]

Strauss et al.

[11] Patent Number: 4,471,765
[45] Date of Patent: Sep. 18, 1984

[54] APPARATUS FOR RADIOLABELING RED BLOOD CELLS

[75] Inventors: Harry W. Strauss, Newton; Ronald J. Callahan, Boston; Jerry W. Froelich, Woburn, all of Mass.

[73] Assignee: The Massachusetts General Hospital, Boston, Mass.

[21] Appl. No.: 386,661

[22] Filed: Jun. 25, 1982

Related U.S. Application Data

[62] Division of Ser. No. 190,667, Sep. 25, 1980, Pat. No. 4,372,294.

[51] Int. Cl.³ .............................................. A61B 6/00
[52] U.S. Cl. .................................... 128/1.1; 128/655; 604/181; 604/232; 604/191
[58] Field of Search ............... 604/181, 187, 191, 199, 604/232, 236; 128/1.1, 1.2, 654, 655

[56] References Cited

U.S. PATENT DOCUMENTS

| | | | |
|---|---|---|---|
| 2,393,576 | 1/1946 | Thomas | 604/181 |
| 2,804,075 | 8/1957 | Borden | 604/269 |
| 3,063,449 | 11/1962 | Schultz | 604/181 |
| 3,784,453 | 1/1974 | Dworkin et al. | 128/1.1 X |
| 4,300,569 | 2/1980 | Bonneau | 128/654 |
| 4,364,376 | 12/1982 | Bigham | 128/1.1 |
| 4,372,294 | 2/1983 | Strauss et al. | 128/1.1 |

Primary Examiner—Dalton L. Truluck
Attorney, Agent, or Firm—Paul J. Cook

[57] ABSTRACT

A method and apparatus for radiolabeling red blood cells is provided which includes a syringe holder, a vial containing heparin, a vial containing technetium-99m and a catheter. The vials and catheter are connected to channels within the syringe holder and a valve positioned at the intersection of the channels is capable of effecting selective communication between the catheter and either vial or none of the vials. The catheter is filled with heparin and a blood sample is drawn from the patient through the catheter and into the vial containing the technetium-99m. The catheter then is filled with heparin and the blood sample is incubated. The labeled red blood cells then are injected into the patient through the catheter.

2 Claims, 2 Drawing Figures

APPARATUS FOR RADIOLABELING RED BLOOD CELLS

This is a division of application Ser. No. 190,667 filed Sept. 25, 1980, now U.S. Pat. No. 4,372,294.

BACKGROUND OF THE INVENTION

This invention relates to a method and apparatus for radiolabeling red blood cells.

Radioscanning and similar radiographic techniques are used increasingly in biological medical research and diagnostic procedures. Radioscanning procedures involve the preparation of radioactive media which, upon injection, infusions or otherwise introduced into a biological subject, become localized in specific organs, tissue or skeletal material or remain in the blood stream which are under study. Traces, plots or so-called "photographs" of the distribution of the radioactive material may be made by various radioscanning means, such as radiodetection rays, traversing scanners, scintillation cameras or the like. The resultant distribution in corresponding relative intensity would then be used to indicate the presence of aberrations, pathological conditions or the like.

Technetium-99m (Tc-99m) recently has gained wide acceptance as a tagging moiety. The value of technetium-99m for clinical scintiscanning stems both from its physical and from its chemical properties. Its short half-life, of 6 hours, coupled with an absence of primary $\beta$-emission, result in very low radiation doses to tissues. The high activities can therefore be administered in as short a time required for a scan and enables several views of the area of the body being examined. The low energy of the gamma-emission, 140 KeV enables a picture to be obtained with a focusing collimator, of virtually a surface layer a few cm in thickness. This is due partly to improved resolution and partly to reduction in the contribution of radiation from deeper structures by self-absorption.

Prior to the present invention, red blood cells have been labeled with technetium-99m in order to provide visualization of the blood pools and the spleen in a patient. Labeling methods include both in vitro techniques and in vivo techniques. The in vitro techniques are undesirable since they are cumbersome and time-consuming. The in vivo techniques generally utilized comprise the sequential injection of stannous pyrophosphate followed by injection of technetium-99m as pertechnetate approximately 30 minutes later. Unfortunately, the procedure results in relatively incomplete radiolabeling of red blood cells and results in gastric visualization in some patients that causes undesirable background which reduces visualization of the blood.

Accordingly, it would be desirable to provide a means for labeling red blood cells which minimizes gastric visualization and improves the efficiency of labeling as compared to the efficiency of present methods for labeling red blood cells. Furthermore, it would be desirable to provide such a means which eliminates the cumbersome manipulation procedures required in presently employed in vivo processes for labeling red blood cells.

SUMMARY OF THE INVENTION

The present invention provides an apparatus which permits both obtaining a blood sample from a patient previously injected with a reducing agent for pertechnetate and admixing the sample with technetium-99m under conditions such that the blood does not become coagulated or contaminated. Thereafter, the apparatus is activated to inject the mixture of blood and technetium-99m into the patient's bloodstream so that the patient's blood pool can be monitored.

DESCRIPTION OF SPECIFIC EMBODIMENTS

In accordance with this invention, the process and apparatus is provided which decreases background radioactivity from free technetium and minimizes gastric excretions of technetium as compared to presently available processes for labeling red blood cells. The patient first is injected with a reducing agent for pertechnetate which comprises stannous ion utilizing Stannous Pyrophosphate or the like as the source in a physiologically acceptable solution and at a concentration which provides effective reduction of pertechnetate without toxicity to the patient. Generally, the amount of reducing agent is typically about 700 $\mu$g Sn$^{++}$, about 500 $\mu$g Sn$^{++}$ to about 1000 $\mu$g Sn$^{++}$. Approximately 20 to 30 minutes after the injection of the reducing agent, the apparatus of this invention which includes a catheter filled with a heparin solution is applied to the patient and the catheter is inserted into the patient's vein. The heparin solution also is present in a valve which controls the flow of heparin, technetium-99m and blood through the apparatus of this invention including the catheter. A syringe containing technetium-99m as pertechnetate is connected with the valve and the heparin within the apparatus is drawn into the syringe containing the technetium-99m followed by a blood sample from the patient which enters the syringe containing the blood and technetium-99m and to communicate with a second syringe containing heparin which then is injected into the catheter and the valve in order to prevent coagulation of the blood which is to be subsequently passed from the syringe into the catheter back into the patient. The syringe containing the blood and technetium-99m then is gently agitated for a period of about 5 to 10 minutes or more in order to label the red blood cells therein with technetium-99m. By replacing the thermal insulator (28) with a thermostatically controlled heating jacket, the temperature of the syringe can be raised to 49°–50° C. for 35 minutes. When operated in this manner a selective spleen scanning radiopharmaceutical is prepared. Thereafter, the valve is positioned in order to close the syringe containing the heparin and to open the syringe containing the labeled red blood cells. The labeled red blood cells then are reinjected into the patient as a bolus preceded by the heparin in the catheter. The patient then is monitored to follow the flow of the labeled red blood cells through the patient.

Figure 1:
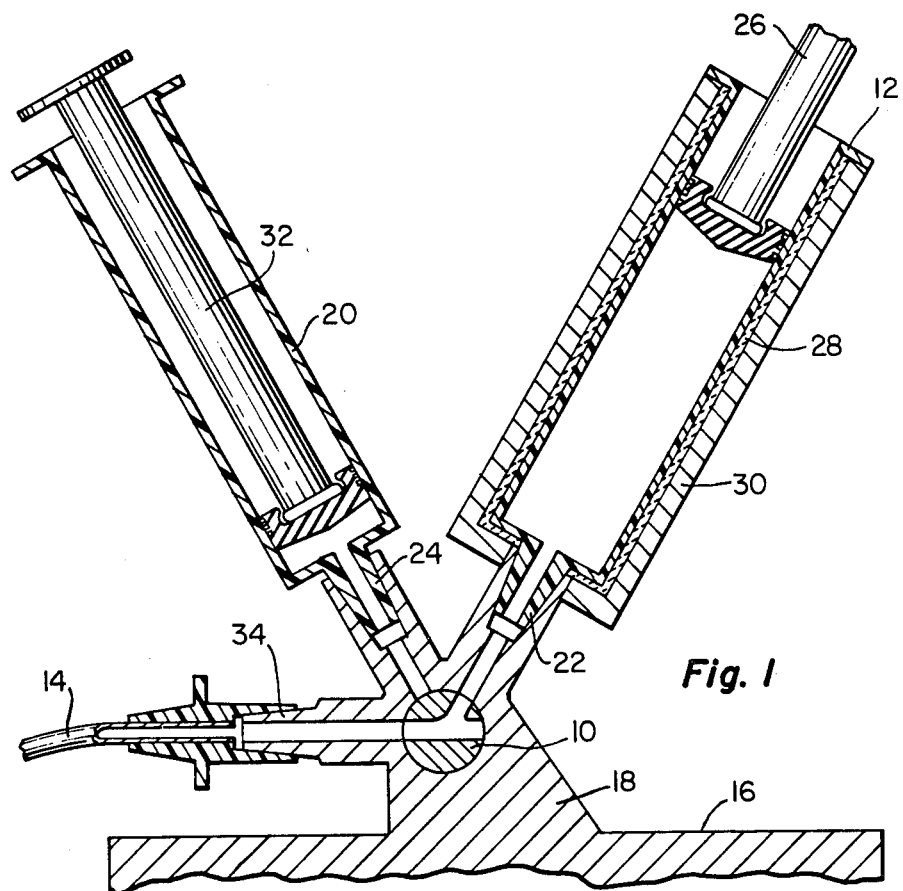
FIG. 1 is a cross-sectional view of the apparatus of this invention.

Referring to the drawing, FIG. 1 shows the apparatus of this invention with the valve 10 in position to effect communication between syringe 12 and catheter 14. The apparatus includes a base 16 to provide support and a syringe holder 18 to which can be attached syringe 12, syringe 20 and catheter 14. Syringe 12 having a tapered end 22 is press fit into the syringe holder 18. Similarly, syringe 20 is press fit into syringe holder 18 by means of a tapered head 24. The syringe 12 contains technetium-99m as pertechnetate preferably as a sodium salt and is maintained at its physiological pH in a manner well known in the art. Only a portion of the syringe 12 is filled with the pertechnetate solution so that heparin within the catheter and a blood sample can be subsequently drawn into the syringe 12 to effect radiolabeling of red blood cells. The syringe 12 includes a conventional plunger 26 so that liquid can be drawn into and injected from syringe 12. The syringe 12 also optionally can be surrounded by a thermal insulating layer 28 so that the proper temperature of the blood and the syringe 12 can be maintained during radiolabeling. In addition, the syringe 12 optionally can include a shield material 30 to absorb radiation from the technetium-99m during red blood cell radiolabeling. The syringe 20 includes a conventional plunger 32. The catheter 14 is attached to syringe holder 18 by being press fit on tapered head 34.

The valve 10, such as a 4-way stopcock, is adapted to be positioned to shut off both syringes 12 and 20 from communication with catheter 14 or to selectively open communication between catheter 14 and either one of syringes 12 or 20. Communication between the catheter 14 and syringe 12 can be effected by the valve position shown in FIG. 1, while communication between catheter 14 and syringe 20 can be effected by means of the valve positioning shown in FIG. 2.

Figure 2:
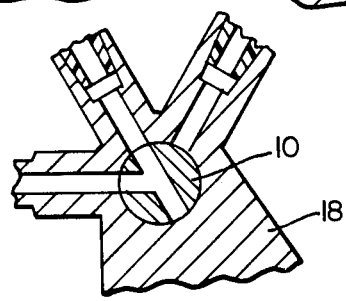
FIG. 2 shows the position of the stopcock shown in FIG. 1 when the apparatus is heparinized.

After the patient has been injected with a reducing composition, the catheter 14 is filled with heparin from syringe 20 and injected into the patient's vein. The catheter is filled with heparin when the valve is in the position as shown in FIG. 2. Thereafter, the valve 10 is positioned as shown in FIG. 1 and the plunger 26 is drawn upwardly in order to draw the heparin within the catheter 14 into syringe 12 and to draw a blood sample from the patient into the syringe 12. Typically, the blood sample comprises between about 3 and 10 cubic centimeters while the amount of technetium-99m is between about 15 and 25 mCi, preferably about 20 mCi. The valve 10 then is positioned in order to close communication between catheter 14 and syringe 12 and to open communication between syringe 20 and catheter 14. The plunger 32 then is depressed in order to fill the catheter 14 and the channels within the valve 10 with heparin so that blood subsequently passing therethrough will not coagulate. After a suitable incubation time, we can substantially complete labeling of the red blood cells. The valve 10 in position as shown in FIG. 1 and the plunger 26 is depressed in order to inject the patient with a bolus comprising the heparin within the catheter 14 and the composition within syringe 12 including the labeled red blood cells.

A kit can be prepared which can be utilized to perform the process of this invention. The kit includes the syringe holder and a valve capable of functioning as described above, a vial containing saline to which can be added technetium-99m as petechnetate and a vial containing reducing stannous composition. Each vial is provided with means by which it can be attached to the syringe holder in communication with the valve such as tapered fittings. The kit optionally can include a vial containing heparin. In use, the kit can be utilized in the manner supported above wherein the vial containing the stannous reducing agent is first placed on the syringe holder and is injected into the patient. Thereafter, the vial containing the saline to which has been added technetium-99m is positioned on the holder and utilized in the manner set forth above.

The following example illustrates the present invention and is not intended to limit the same.

EXAMPLE I

Seven randomly selected patients undergoing cardiac gated blood pool imaging had 10 ml of blood drawn into the heparinized syringe shown in FIGS. 1 and 2 with syringe 12 containing 25 mCi of technetium-99m as pertechnetate. Twenty minutes prior to drawing the blood, each patient was injected with stannous pyrophosphate containing 700 $\mu$g $Sn^{++}$ in 3 cc saline. The blood and pertechnetate were allowed to incubate for 10 minutes with gentle shaking. The catheter 14 was filled with heparin by means of syringe 20. Thereafter, the blood containing radiolabeled red blood cells was reinjected into each patient. To determine the kinetics of labeling within the syringe, aliquots were removed from syringe 12 at one minute intervals into tubes containing stannous DTPA (SN-DTPA) which instantaneously stops the labeling of red blood cells by chelation with unbound technetium-99m. At ten minutes, the labeling efficiency was 88% (n=4). To determine whether this approach reduced gastric visualization in patients, this group was compared with six randomly selected patients undergoing standard in vivo labeling. There was no gastric visualization in six of the seven patients who were injected by the technique of this invention, whereas there was gastric visualization of five of the six patients injected with the standard in vivo technique.

We claim:

1. An apparatus for radiolabeling red blood cells which comprises a syringe holder having a plurality of channels capable of being opened or closed by a valve located at the intersection of said channels, a catheter attached to the exit of one of said channels, a vial containing heparin attached to another of said channels and a vial containing technetium-99m attached to a third channel, said valve being capable of selectively providing communication between said catheter and only one of said vials, means associated with each of said vials for drawing or removing liquid from said vials, and means for drawing blood from a patient, mixing said blood with heparin in said catheter and introducing said mixture of heparin and blood into the vial containing technetium-99m.

2. The apparatus of claim 1 wherein said vial containing technetium-99m includes thermal insulation surrounding said vial and a shield for absorbing radioactive emissions surrounding said thermal layer.

* * * * *